(12) United States Patent
Koike et al.

(10) Patent No.: US 6,787,662 B2
(45) Date of Patent: Sep. 7, 2004

(54) FLUORINATED ORGANOSILICON COMPOUNDS

(75) Inventors: Noriyuki Koike, Gunma-ken (JP); Hiromasa Yamaguchi, Gunma-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/287,669

(22) Filed: Nov. 5, 2002

(65) Prior Publication Data

US 2003/0120100 A1 Jun. 26, 2003

(30) Foreign Application Priority Data

Nov. 5, 2001 (JP) ........................................ 2001-338983

(51) Int. Cl.$^7$ ................................................. C07F 7/04
(52) U.S. Cl. ...................................................... 556/451
(58) Field of Search .......................................... 556/451

(56) References Cited

U.S. PATENT DOCUMENTS 4,032,502 A * 6/1977 Lee et al. .................... 523/212

FOREIGN PATENT DOCUMENTS

JP 3-197484 A 8/1991

OTHER PUBLICATIONS

Chemical Abstracts 1965:432464: Abstrarct of Patent NL 6411638, Dow Corning Corp.*

* cited by examiner

Primary Examiner—Samuel Barts
(74) Attorney, Agent, or Firm—Birch, Stewart, Kolasch & Birch, LLP

(57) ABSTRACT

Fluorinated organosilicon compounds having perfluoroalkyl or perfluorooxyalkyl radicals and at least four SiH radicals are highly compatible with base polymers having high fluorine contents and useful as a crosslinking agent therefor to produce addition cured rubber having desired hardness and modulus.

20 Claims, 1 Drawing Sheet

FLUORINATED ORGANOSILICON COMPOUNDS

This nonprovisional application claims priority under 35 U.S.C. § 119(a) on Patent Application No. 2001-338983 filed in JAPAN on Nov. 5, 2001, which is herein incorporated by reference.

This invention relates to novel fluorinated organosilicon compounds useful as a crosslinking agent in addition reaction.

BACKGROUND OF THE INVENTION

Rubber compositions of the addition reaction curing type generally contain a base polymer having alkenyl radicals such as vinyl, a compound having at least three hydrogen atoms directly attached to silicon atoms (i.e., SiH radicals), and an addition reaction catalyst such as platinum catalyst. The compositions cure through addition reaction of SiH radicals to alkenyl radicals on the base polymer.

Known fluorinated organosilicon compounds having SiH radicals include those compounds of the structure wherein three SiH radicals are attached via oxygen atoms to a Si atom having a fluoroalkyl substituent radical as shown below (JP-A 3-197484).

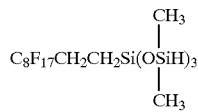

By virtue of fluoroalkyl radicals, these compounds are compatible with base polymers having high fluorine contents. They are very useful as a crosslinking agent particularly when combined with base polymers in the form of terminally modified perfluoropolyether.

Physical properties of cured rubber compositions of the addition reaction curing type, especially hardness and modulus are governed by the molecular weight of the base polymer and the number per molecule of SiH radicals in the crosslinking agent. As long as the same base polymer is used, the use of the above-mentioned compounds as a crosslinking agent always results in cured rubbers having a limited range of hardness and modulus.

SUMMARY OF THE INVENTION

An object of the invention is to provide a fluorinated organosilicon compound having at least four SiH radicals which is highly compatible with base polymers having high fluorine contents.

We have found that fluorinated organosilicon compounds containing fluoroalkyl radicals and at least four SiH radicals per molecule as represented by the formula (1) below are obtained by co-hydrolysis of a trichlorosilane having a fluoroalkyl substituent radical and dimethylchlorosilane, and that these fluorinated organosilicon compounds are highly compatible with base polymers having high fluorine contents.

The invention provides a fluorinated organosilicon compound of the following general formula (1).

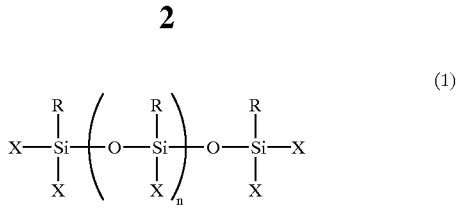

Herein R is independently $-(CH_2)_a$-Rf wherein Rf is a monovalent perfluoroalkyl or perfluorooxyalkyl radical having 1 to 12 carbon atoms, and "a" is 2 or 3, X is $-OSi(CH_3)_2H$, and n is 0 or 1.

DESCRIPTION OF THE PREFERRED EMBODIMENT

Figure 1:
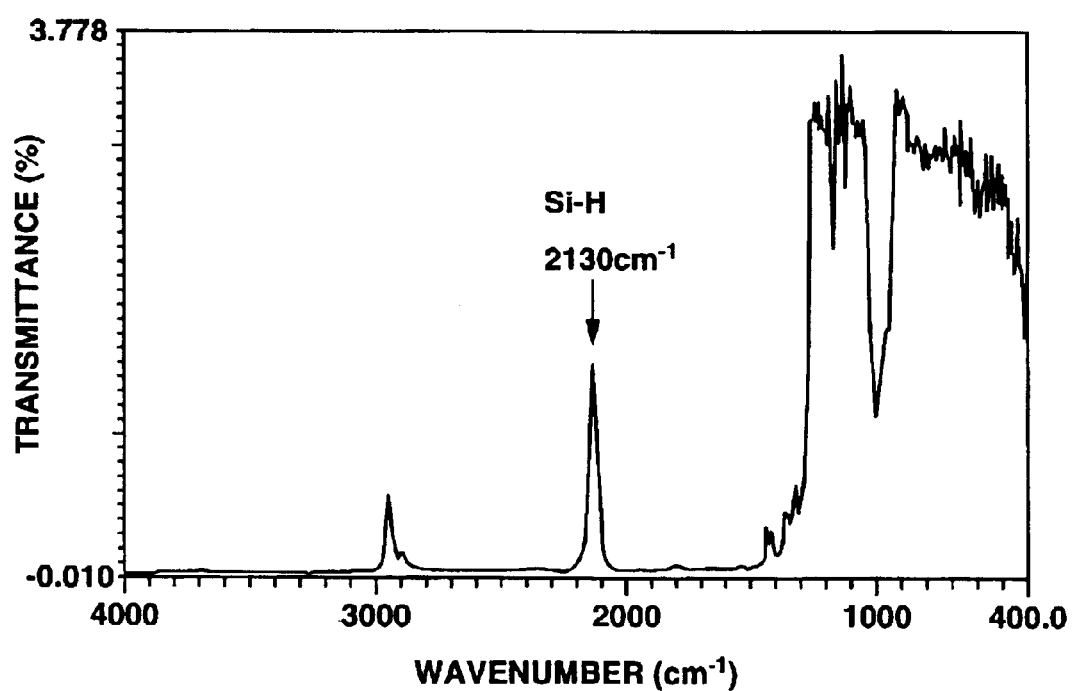
FIG. 1 is an IR analysis chart of component B obtained in Example 1.

The fluorinated organosilicon compounds of the invention have the general formula (1).

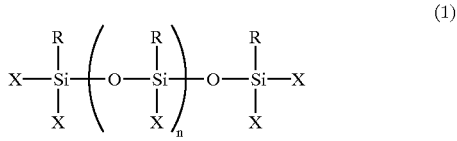

In formula (1), R is independently $-(CH_2)_a$-Rf wherein Rf is a monovalent perfluoroalkyl or perfluorooxyalkyl radical having 1 to 12 carbon atoms, and "a" is 2 or 3. Those radicals having 4 to 12 carbon atoms are preferred as R because the resulting compounds are more compatible with base polymers having high fluorine contents. Examples of R are shown below.

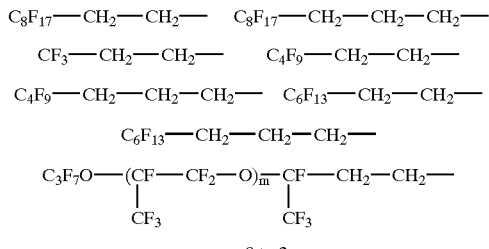

X is $-OSi(CH_3)_2H$, and n is 0 or 1.

The fluorinated organosilicon compounds of the invention can be synthesized by co-hydrolysis of a trichlorosilane having a fluoroalkyl or fluorooxyalkyl substituent radical and dimethylchlorosilane. Examples of the trichlorosilane having a fluoroalkyl or fluorooxyalkyl radical are given below.

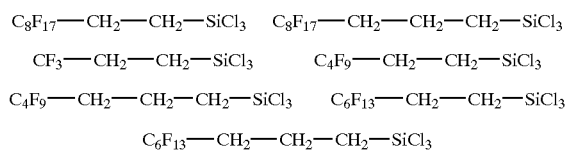

-continued

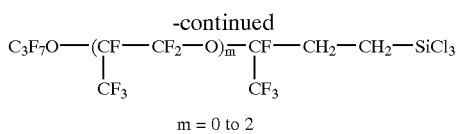

m = 0 to 2

Co-hydrolysis can be carried out by adding dropwise a mixture of a trichlorosilane having a fluoroalkyl or fluorooxyalkyl radical and dimethylchlorosilane to aqueous hydrochloric acid. The trichlorosilane and dimethylchlorosilane are mixed in such a preferred ratio that 1.2 to 2.5 moles of dimethylchlorosilane is present per mole of the trichlorosilane, and more preferably 1.6 to 2.0 moles of dimethylchlorosilane is present per mole of the trichlorosilane.

The mixture is preferably diluted with a solvent prior to hydrolysis. Suitable solvents include toluene, tetrahydrofuran, 1,3-bistrifluoromethylbenzene and HCFC-225.

The aqueous hydrochloric acid is typically a solution having a concentration of 25 to 35%. The amount of aqueous hydrochloric acid used is not critical as long as hydrochloric acid generated by hydrolysis reaction can be dissolved therein (the solution is not over-saturated at the reaction temperature).

For effective hydrolysis, a mixture of a trichlorosilane having a fluoroalkyl or fluorooxyalkyl radical and dimethylchlorosilane, preferably diluted, may be added dropwise to a hydrochloric acid aqueous solution while stirring the solution. During the addition, the temperature is preferably kept in the range of −20° C. to 10° C. Temperatures higher than 10° C. can promote side reaction, reducing the yield of the end product. At the end of dropwise addition, while keeping the temperature in the above range, stirring is continued for 1 to 2 hours until the reaction is completed.

After the completion of reaction, the reaction mixture is poured into ice water to dilute the hydrochloric acid. The organic phase is then washed with water to remove the acid contents. The solvent is stripped, yielding a mixture containing fluorinated organosilicon compounds within the scope of the invention. The end compound can be isolated by suitable techniques such as distillation, extraction and column chromatography.

The fluorinated organosilicon compounds of the invention are not only useful as a crosslinking agent in addition reaction, but are also utilized in other applications, for example, as modifier intermediates.

EXAMPLE

Examples of the invention are given below by way of illustration and not by way of limitation.

Example 1

A 500-ml four-necked flask equipped with a thermometer and stirrer was charged with 240 g of a 35% hydrochloric acid aqueous solution and 40 g of tetrahydrofuran and cooled with a refrigerant so that the internal temperature became −12° C. Then, a mixture of 80.0 g of $C_8F_{17}CH_2CH_2SiCl_3$, 26.0 g of dimethylchlorosilane and 120 g of 1,3-bistrifluoromethylbenzene was added dropwise over 1 hour. The internal temperature was kept at −12° C. to −8° C. during the dropwise addition. After the completion of addition, stirring was continued for a further 1.5 hours at −12° C. to −10° C.

The reaction mixture was then poured into 1 liter of ice water, which was thoroughly agitated. The organic phase was separated therefrom and washed with water. The solvent was distilled off, yielding 82.0 g of a reaction mixture.

On analysis by gas chromatography, the reaction mixture was found to contain the following three compounds.

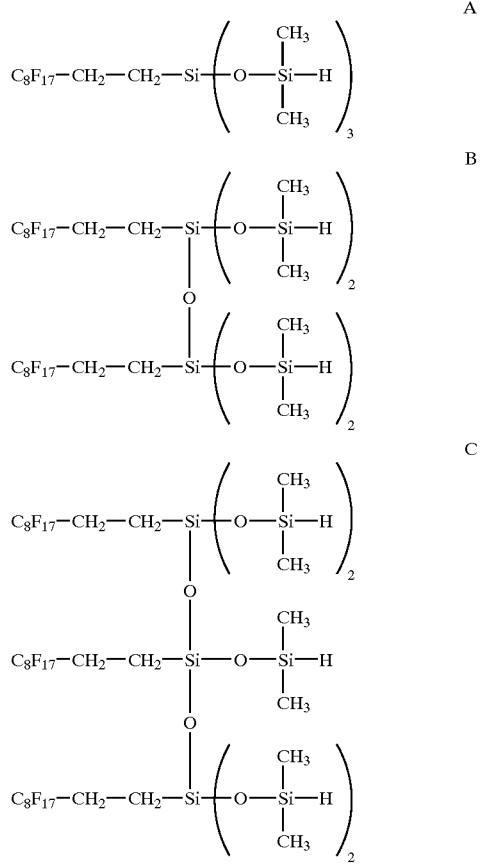

The contents by GC and boiling points of the respective compounds are shown below.

| Structure | Content (%) | b. p. |
|---|---|---|
| A | 38.4 | 92–94° C./4 mmHg |
| B | 25.6 | 175–189° C./mmHg |
| C | 11.7 | — |
| others | 24.3 | — |

The NMR spectral data of isolated component B are shown below, and the chart of IR analysis is shown in FIG. 1.

Results of $^1$H-NMR analysis (TMS standard, ppm)

| | δ chemical shift (ppm) | Integration ratio |
|---|---|---|
| Si—CH$_3$ | 0.05 | 6.00 |
| Si—CH$_2$ | 0.63 | 1.08 |
| CF$_2$—CH$_2$ | 2.00 | 1.06 |
| Si—H | 4.61 | 1.00 |

There have been described fluorinated organosilicon compounds having at least four SiH radicals which are highly compatible with base polymers having high fluorine contents and useful as a crosslinking agent therefor to produce addition cured rubber having desired hardness and modulus.

Japanese Patent Application No. 2001-338983 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A fluorinated organosilicon compound of the following general formula (1):

$$X-\underset{\underset{X}{|}}{\overset{\overset{R}{|}}{Si}}-\left(O-\underset{\underset{X}{|}}{\overset{\overset{R}{|}}{Si}}\right)_n-O-\underset{\underset{X}{|}}{\overset{\overset{R}{|}}{Si}}-X \quad (1)$$

wherein R is independently —(CH$_2$)$_a$—Rf wherein Rf is a monovalent perfluoroalkyl or perfluorooxyalkyl radical having 4 to 12 carbon atoms, and "a" is 2 or 3, X is —OSi(CH$_3$)$_2$H, and n is 0 or 1.

2. The fluorinated organosilicon compound of claim 1, wherein R is selected from the group consisting of C$_8$F$_{17}$—CH$_2$—CH$_2$—,  C$_8$F$_{17}$—CH$_2$—CH$_2$—CH$_2$—,
C$_4$F$_9$—CH$_2$—CH$_2$—,  C$_4$F$_9$—CH$_2$—CH$_2$—CH$_2$—,
C$_6$F$_{13}$—CH$_2$—CH$_2$—,  C$_6$F$_{13}$—CH$_2$—CH$_2$—CH$_2$—  and
C$_3$F$_7$O—(CF—CF$_2$—O)$_m$-CF—CH$_2$—CH$_2$—
                |                          |
               CF$_3$                    CF$_3$ wherein m is 0 to 2.

3. The fluorinated organosilicon compound of claim 1, wherein n is 1.

4. A method of making a fluorinated organosilicon compound of the following formula (1)

$$X-\underset{\underset{X}{|}}{\overset{\overset{R}{|}}{Si}}-\left(O-\underset{\underset{X}{|}}{\overset{\overset{R}{|}}{Si}}\right)_n-O-\underset{\underset{X}{|}}{\overset{\overset{R}{|}}{Si}}-X \quad (1)$$

wherein R is independently —(CH$_2$)$_a$—Rf wherein Rf is a monovalent perfluoroalkyl or perfluorooxyalkyl radical having 4 to 12 carbon atoms, and "a" is 2 or 3, X is —OSi(CH$_3$)$_2$H, and n is 0 or 1;

comprising co-hydrolyzing a trichlorosilane having a fluoroalkly or fluorooxyalkyl substituent radical and dimethylchlorosilane.

5. The method according to claim 4, wherein the trichlorosilane having a fluoroalkyl or fluorooxyalkyl radical is selected from the group consisting of:

C$_8$F$_{17}$—CH$_2$—CH$_2$—SiCl$_3$,  C$_8$F$_{17}$—CH$_2$—CH$_2$—CH$_2$—SiCl$_3$,
CF$_3$—CH$_2$—CH$_2$—SiCl$_3$,  C$_4$F$_9$—CH$_2$—CH$_2$—CH$_2$—SiCl$_3$,
C$_6$F$_{13}$—CH$_2$—CH$_2$—SiCl$_3$,
C$_6$F$_{13}$—CH$_2$—CH$_2$—CH$_2$—SiCl$_3$  and
C$_3$F$_7$O—(CF—CF$_2$—O)$_m$-CF—CH$_2$—CH$_2$—SiCl$_3$
              |                            |
             CF$_3$                      CF$_3$ wherein m is 0 to 2.

6. The method according to claim 5, wherein m is 1.

7. The method according to claim 5, wherein the co-hydrolyzing is carried out in aqueous hydrochloric acid.

8. The method according to claim 6, wherein the co-hydrolyzing is carried out in aqueous hydrochloric acid.

9. The method according to claim 5, wherein a ratio of the trichlorosilane having a fluoroalkly or fluorooxyalkyl substituent radical to the dimethylchlorosilane is 1 mole of the trichlorosilane to 1.2 to 2.5 moles of dimethylchlorosilane.

10. The method according to claim 6, wherein a ratio of the trichlorosilane having a fluoroalkly or fluorooxyalkyl substituent radical to the dimethylchlorosilane is 1 mole of the trichlorosilane to 1.2 to 2.5 moles of dimethylchlorosilane.

11. The method according to claim 7, wherein a ratio of the trichlorosilane having a fluoroalkly or fluorooxyalkyl substituent radical to the dimethylchlorosilane is 1 mole of the trichlorosilane to 1.2 to 2.5 moles of dimethylchlorosilane.

12. The method according to claim 5, further comprising a step of diluting the trichlorosilane having a fluoroalkly or fluorooxyalkyl substituent radical and the dimethylchlorosilane in a solvent prior to co-hydrolysis.

13. The method according to claim 6, further comprising a step of diluting the trichlorosilane having a fluoroalkly or fluorooxyalkyl substituent radical and the dimethylchlorosilane in a solvent prior to co-hydrolysis.

14. The method according to claim 7, further comprising a step of diluting the trichlorosilane having a fluoroalkly or fluorooxyalkyl substituent radical and the dimethylchlorosilane in a solvent prior to co-hydrolysis.

15. The method according to claim 12, wherein the solvent is selected from the group consisting of toluene, tetrahydrofuran, 1,3-bistrifluoromethylbenzene, and HCFC-225.

16. The method according to claim 13, wherein the solvent is selected from the group consisting of toluene, tetrahydrofuran, 1,3-bistrifluoromethylbenzene, and HCFC-225.

17. The method according to claim 14, wherein the solvent is selected from the group consisting of toluene, tetrahydrofuran, 1,3-bistrifluoromethylbenzene, and HCFC-225.

18. The method according to claim 7, wherein a concentration of aqueous hydrochloric acid is from 25 to 35%.

19. The fluorinated organosilicon compound according to claim 1, wherein R is C$_8$F$_{17}$—CH$_2$—CH$_2$—.

20. The fluorinated organosilicon compound according to claim 3, wherein R is C$_8$F$_{17}$—CH$_2$—CH$_2$—.

* * * * *